United States Patent
Ding et al.

(10) Patent No.: US 11,571,453 B2
(45) Date of Patent: Feb. 7, 2023

(54) PIPER LAETISPICUM EXTRACT AND PREPARATION METHOD THEREFOR AND USE THEREOF

(71) Applicant: SUZHOU YI-HUA BIOMEDICAL TECHNOLOGY CO., LTD, Suzhou (CN)

(72) Inventors: Xiujuan Ding, Suzhou (CN); Wu Chen, Suzhou (CN); Yi Jiang, Suzhou (CN); Yongbao Li, Suzhou (CN)

( * ) Notice: Subject to any disclaimer, the term of this patent is extended or adjusted under 35 U.S.C. 154(b) by 150 days.

(21) Appl. No.: 16/760,045

(22) PCT Filed: Oct. 29, 2018

(86) PCT No.: PCT/CN2018/112318
§ 371 (c)(1),
(2) Date: Apr. 29, 2020

(87) PCT Pub. No.: WO2019/085847
PCT Pub. Date: May 9, 2019

(65) Prior Publication Data
US 2021/0187051 A1   Jun. 24, 2021

(30) Foreign Application Priority Data

Nov. 1, 2017 (CN) .......................... 201711072049.8

(51) Int. Cl.
| *A61K 36/67* | (2006.01) |
| *A61P 25/22* | (2006.01) |
| *A61P 25/24* | (2006.01) |
| *A61K 9/00* | (2006.01) |
| *A61K 31/166* | (2006.01) |
| *A61K 31/357* | (2006.01) |

(52) U.S. Cl.
CPC ............ *A61K 36/67* (2013.01); *A61K 9/0053* (2013.01); *A61K 31/166* (2013.01); *A61K 31/357* (2013.01); *A61P 25/22* (2018.01); *A61P 25/24* (2018.01); *A61K 2236/10* (2013.01); *A61K 2236/333* (2013.01); *A61K 2236/51* (2013.01)

(58) Field of Classification Search
None
See application file for complete search history.

(56) References Cited

U.S. PATENT DOCUMENTS 8,062,678 B2 * 11/2011 Wang ..................... A61P 25/24
424/725

FOREIGN PATENT DOCUMENTS

| CN | 1532182 A | 9/2004 |
| CN | 107837301 A | 3/2018 |

OTHER PUBLICATIONS

English translation of the Written Opinion of the Internation Searching Authority for PCT/CN2018/112318; dated Jan. 25, 2019.*
Yuan Yang, International search report and written opinion by CNIPA as the International search authority, dated Jan. 25, 2019.
Xie, Jing et al., "Chemical Constituent in Leaves of Piper Aetispicum", Chinese Herbal Medicines, p. 1536-1539, vol. 40, No. 10, Oct. 31, 2009.

* cited by examiner

*Primary Examiner* — Susan Hoffman
(74) *Attorney, Agent, or Firm* — OPES IP Consulting Co. Ltd.

(57) ABSTRACT

Disclosed are a *Piper laetispicum* extract and a preparation method therefor and a use thereof. The *Piper laetispicum* extract includes any one or more of sesamin, (2E,6E)-N-isobutyl-7-(3,4-methylenedioxyphenyl)heptadienamide, (2E,4E)-N-isobutyldodecane-2,4-dieneamide, (2E,4E)-N-isobutyl-15-phenylpentadeca-2,4-dieneamide, (2E,4E,14Z)—N-isobutyleicosane-2,4,14-trienamide, and (2E,4E)-N-isobutyl-13-phenyltrideca-2,4-dieneamide. The *Piper laetispicum* extract can prevent depression.

12 Claims, No Drawings

PIPER LAETISPICUM EXTRACT AND PREPARATION METHOD THEREFOR AND USE THEREOF

CROSS REFERENCE TO RELATED APPLICATIONS

This application claims priority to PCT Application PCT/CN2018/112318 filed on Oct. 29, 2018, which claims priority to China Application No. 201711072049.8 filed on Nov. 1, 2017, the content of which is incorporated herein in its entirety by reference.

FIELD OF THE INVENTION

The present invention belongs to the medical field, in particular relates to a *Piper laetispicum* extract and preparation method therefor and use thereof.

BACKGROUND OF THE INVENTION

*Piper laetispicum* C.DC, a plant of the pepper family, is mainly distributed in Guangdong, Guangxi, Yunnan, and Hainan provinces of China. It is used by the folk to promote blood circulation, swelling and pain relief, and to treat bruises or bruises.

Depression has become one of the most important diseases that impede human health. About 12% to 25% of people in the world will face depression in their lifetime. As a common global disease, it is currently estimated that about 350 million patients are suffering from depression, and the age distribution has also moved from covering all ages to a younger age.

After years of systematic research, according animal experiments and clinical experiments the applicant has found that the extracts of *Piper laetispicum* have significant antidepressant activity, as well as certain anti-anxiety, analgesic, and sedative biological activities. Two related Chinese invention patents and many international patents have been filed.

At present, the main patents relate to the research on *Piper laetispicum* are filed as following: ZL03115911.7, Preparation of effective parts of *Piper laetispicum* and its application in the medical and health fields; ZL200410084791.7, A method for preparing the extract of *Piper laetispicum*, extracts and uses thereof; ZL201010556017.7, Preparation method of effective compounds of *Piper laetispicum*; ZL201010169679.9, Application of 5'-methoxy-3',4'-hyperdimethoxycinnamic acid isobutylamide in the preparation of antidepressants; 201010296974.0, The preparation method, extract and application of *Piper laetispicum* extract; ZL201110123076.X, An amide compound and the preparation method and application thereof.

Skilled person in the art could know that, for the preparation process of the extract of the effective part of the natural medicine, the parts of the medicinal materials used and the preparation process parameters are different, and the material basis of the obtained extract is different. Such as:

(I) Disclosed in patent ZL201010169679.9, 5'-methoxy-3',4'-methylenedioxycinnamic acid isobutylamide is prepared by the following preparation method:

Step 1: Take the above-ground part of the medicinal pepper plant *Piper laetispicum* or *Piper austrosinense* Tseng, crush coarsely, then place into an extraction tank, add 10~15 times the weight of 70%~95% ethanol, and reflux for 2 hours. Then add 10 to 15 times the weight of 70%~95% ethanol, reflux for 2 hours, filter, combine the two filtrates and concentrate at 65° C. under reduced pressure to an extract with RD1.3-1.35;

Step 2: Dissolve the extract with 30%~60% ethanol, load onto the column of D101 macroporous adsorption resin, and elute with 30%~60% ethanol with the eluent abandoned. And then elute with 70%~95% ethanol, collect the eluent, concentrate to dryness to obtain a concentrate;

Step 3: Mix the concentrate, load onto a chromatography column filled with silica gel, and elute twice with a volume ratio of 5:1 and 3:1 petroleum ether-ethyl acetate. Detect with Thin layer chromatography, combine single-point compound of the largest sample volume under the 3:1 system, recover the solvent, concentrate until no liquid left, yellow particles are precipitated. Wash the yellow particles until becoming white particles with petroleum ether, and then recrystallize with the ethanol-water system to obtain white crystals of 5'-methoxy-3',4'-Methedioxycinnamic acid isobutylamide.

(II) Disclosed in patent ZL201110123076.X, 1-[(2E,4E,7E)-9-(3,4-Methedioxybenzene) nine carbon diallyl]tetrahydropyrrole and 1-[(2E,7E)-N-7-(3,4-Methedioxybenzene) nonacarbodienoyl]tetrahydropyrrole are prepared by the following preparation method:

Step (1) Cut the upper part of *Piper laetispicum* into slices, add 4 to 10 times the volume of 70%~95% ethanol and then reflux for 1.5 to 3.5 hours, filter, and continue to decoct with 3~8 times the amount of ethanol for 1~3 hours, filter, combine the filtrate, recover ethanol under reduced pressure, and concentrate to obtain a extract with relative density of 1.30~1.38 at 60° C.;

Step (2) Dissolve the extract with alcohol aqueous solution, pass through an AB-8 macroporous adsorption resin column, in which the weight ratio of the original medicinal material to the macroporous resin is 5:1~1:1, first elute with 3~8 times the volume of the column bed Rinse with 50% ethanol, and then elute with 2-8 times the amount of 70%-95% ethanol. The eluent is concentrated to obtain an extract, separate the extract by a silica gel column chromatography in which mobile phase is petroleum ether-ethyl acetate 6:1~1:2, obtain the mixture;

Step (3) The mixture is separated by high-efficiency preparation liquid chromatography to obtain 1-[(2E,4E,7E)-9-(3,4-methylenedioxybenzene) nonacarbadienoyl]tetrahydropyrrole and 1-[(2E,7E)-N-7-(3,4-Methedioxybenzene) nine-carbon dienoyl]tetrahydropyrrole.

(III) Disclosed in patent ZL03115911.7, 5'-methoxy-3',4'-methylenedioxycinnamic acid isobutylamide, 3',4'-methylenedioxycinnamic acid isobutylamide, N-isobutyldec-trans-2-trans-4-dienamide, 1-[(2E,4E)-2,4-decadienoyl]tetrahydropyrrole, N-isobutyldec-trans-2-trans-4-dieneamide, 1-[(2E)-5-(3,4-Methylenedioxyphenyl)]tetrahydropyrrole, 5'-methoxy-3',4'-methylenedioxycinnamic acid tetrahydropyrrole are prepared by the following preparation method: grind the dried underground part of *Piper laetispicum* into coarse powder, add 60% ethanol solution to impregnate, reflux twice in water bath with about 1 hour each time, filter, combine the filtrate, concentrate under reduced pressure to 14% of the original filtrate volume, and add 30% ethanol to obtain a clear, opaque, dilute solution of ethanol. Subsequently, separate the solution by macroporous adsorption resin column chromatography, elute with 40%, 55% and 80% ethanol solution successively, collect the 80% ethanol eluent, concentrate and dry to obtain the effective part extract, which was detected by HPLC. The content of amide alkaloids in the extract is 68%.

(IV) Disclosed in patent ZL200410084791.7, an extract, including N-isobutyldec-trans-2-trans-4-dienamide, 1-[(2E, 4E)-2,4-decadienoyl]pyrrolidine, 3',4'-methylenedioxycinnamic acid-isobutylamide, 5'-methoxy-3',4'-methylenedioxycinnamic acid, piperamide C5:1(2E), 5'-methoxy-3',4'-methylenedioxycinnamic acid-tetrahydropyrrol e, 4,5-dihydroepiperminine base, piperamide, is prepared by the following preparation method: take 1 kg of the dried roots and rhizomes of *Piper laetispicum*, cut into segments, add about 90% ethanol to impregnate at room temperature for about 48 hours, then add the same concentration of ethanol to 20 L, and percolate to obtain a crude extract. Add 15 L of warm water to the percolate and stir to mix, then load the diluted percolate onto the D101 macroporous adsorption resin column. After flowing through, elute with 40% and 90% ethanol successively. Collect the liquid eluted by 90% ethanol. Concentrate and dry at a temperature not exceeding 70° C. to obtain a refined extract.

(V) Disclosed in patent ZL 201010556017.7, an extract, including [(2E,4E)-N-isobutyl-9-(3,4-methylenedioxybenzene) heptadieneamide, [(2E,4E,7E)-N-isobutyl-9-(3,4-Methedioxybenzene) nonacarbadieneamide, (2E,4E)-N-isobutyl-9-phenyl nonacarbadieneamide, laetispicine, is prepared by the following preparation method: Take the aboveground part of *Piper laetispicum*, coarsely pulverized, add 6 times the amount of 95% ethanol solution, extract under reflux for 2 hours, filter, and extract the residue with 5 times the amount of 95% ethanol under reflux for 2 hours, filter, combine the extracts, concentrate to a concentrated extract under reduced pressure at 60° C., the total extract of *Piper laetispicum* is obtained. Take the total extract of *Piper laetispicum* and dissolve it with 50% ethanol to 1 times the volume of the total extract (dissolve ½ 95% first, dissolve the insoluble matter with ½ hot water, and combine the obtained solution). Load onto D101 macroporous resin, elute with 70% ethanol solution at a flow rate of 1 BV/h. The eluent was collected at 4 BV and discarded. Continue to elute with 95% ethanol at a flow rate of 1 BV/h, collect the eluent 4 BV, and concentrate to a concentrated extract to obtain the effective components of *Piper laetispicum*.

Patent 201010296974.0 discloses a preparation method: take the coarse powder of the roots and canes of *Piper laetispicum*, add 70% ethanol of about 10 times the amount of medicinal materials, percolate at room temperature to obtain a crude extract solution, and then concentrate the crude extract solution under vacuum conditions to about 25% of the original volume. Then the concentrated crude extract solution is stirred evenly and then separated and purified on a large non-polar adsorption resin column, eluted with 30% and 80% ethanol in sequence, and the liquid eluted by 80% ethanol is collected, concentrated and dried to obtain a refined extract. However, it does not disclose which compound are contained in the extract, nor does it separate or identify the specific active compounds in the extract, nor does it measure the content of the active compounds. In fact, what is obtained is a kind of extract with unknown activity.

However, the antidepressant effect of the extracts obtained by the prior preparation methods still need to be improved.

SUMMARY OF THE INVENTION

The technical problem to be solved by the present invention is to provide a *Piper laetispicum* extract with clearly active compounds, good medicinal effects and high safety, and a preparation method and application thereof.

To solve the above technical problems, the present invention provides the following technical solutions:

An object of the present invention is to provide a *Piper laetispicum* extract, including anyone or any combination of more than one of sesamin, (2E,6E)-N-isobutyl-7-(3,4-methylenedioxyphenyl) heptadienamide, (2E,4E)-N-isobutyldodecane-2,4-dieneamide, (2E,4E)-N-isobutyl-15-phenylpentadeca-2,4-dieneamide, (2E,4E,14Z)—N-isobutyleicosane-2,4,14-trienamide, (2E,4E)-N-isobutyl-13-phenyltrideca-2,4-dieneamide.

Further, the *Piper laetispicum* extract also includes anyone or any combination of more than one of 3',4'-methylenedioxycinnamic acid isobutylamide, 5'-methoxy-3',4'-methylenedioxycinnamic acid, N-isobutyldec-trans-2-trans-4-dienamide.

Preferably, the *Piper laetispicum* extract includes sesamin, (2E,6E)-N-isobutyl-7-(3,4-methylenedioxyphenyl) heptadienamide, (2E,4E)-N-isobutyldodecyl-2,4-dienamide, (2E,4E)-N-isobutyl-15-phenylpentadeca-2,4-dienamide, (2E,4E,14Z)—N-isobutyl eicosane-2,4,14-trienamide, (2E,4E)-N-isobutyl-13-phenyltrideca-2,4-di enamide, 3',4'-methylenedioxycinnamic acid isobutylamide, 5'-methoxy-3',4'-methylenedioxycinnamic acid isobutylamide and N-isobutyldecyl-trans-2-trans 4-dienamide.

Preferably, the total mass content of the amide alkaloids in the *Piper laetispicum* extract is 30%-85%.

Another object of the present invention is to provide a preparation method of the *Piper laetispicum* extract. In order to obtain an extract with low impurity content while retaining the active compounds as much as possible, the applicant of the present invention has completed the following preparation process after repeated research. Since most of the amide alkaloid compounds in *Piper laetispicum* are low-polar compounds, water extraction or low-concentration ethanol extraction may lead an incomplete extraction of alkaloids and a high content of impurities, so after comprehensive consideration and repeated tests, the applicant applies a method wherein the volume concentration is 80%~95% ethanol for extraction. Common extraction methods include conventional extraction methods such as decoction, heating reflux, impregnating, and percolation. However, studies found that most amide alkaloids are unstable to heat. The temperature of decoction or heating reflux extraction methods is often difficult to control, which could affect the extraction efficiency. Therefore, it is best to use immersion or percolation for extraction. Studies found that in the process of solvent recovering, some alkaloids will be destroyed due to the temperature, and some alkaloids will not reconstitute after precipitation. Therefore, the temperature of the solvent recovering and the volume and ethanol content of the extract after solvent recovering step could greatly influence on the composition and content of the alkaloid in the extract of the present invention, and also greatly influence on the adsorption effect of the macroporous resin. After comprehensive consideration and repeated tests, the applicant of the present invention has found that when the extraction solution is recovered until the alcohol content reaches 35%~45% and the temperature is less than 70° C. in solvent recovering, the alkaloid obtained from the effective parts is the most complete and the total content is the highest. After the adsorption is completed, it is first eluted with a low concentration ethanol solution so as to remove the impurities adsorbed by the macroporous resin and to retain the effective compounds as much as possible. Therefore, as the upper limit, the concentration of the ethanol in the elution solvent should not to elute the alkaloids. According researches, the applicant of the present invention found that it is most suitable to elute with 30%~50%, 50%~70% ethanol solution in sequence, by which the alkaloid compounds in the present invention are fully retained. And then the alkaloid compounds could be desorbed with 80%~95% ethanol solution. The eluent could be collected and concentrated under reduced pressure to obtain an extract of the effective part of *Piper laetispicum*. The extract comprises not only amide alkaloid compounds but also the lignan compound sesamin. Similarly, when the eluent is concentrated, the temperature should not exceed 70° C.

Therefore, the present invention provides a preparation method of the *Piper laetispicum* extract, including the following steps:

Step (1): After pretreatment of the *Piper laetispicum* material, add 80%~95% ethanol solution of 10~30 times the weight of the material to impregnate or percolate to obtain a crude extract;

Step (2): Concentrate the crude extract obtained in step (1) to an alcohol content of 35%~45%, in which the concentrating temperature is controlled not to exceed 70° C.;

Step (3): Load the crude extract concentrated in step (2) onto the macroporous adsorption resin column, and elute in sequence with 30%~50% and 50%-70% ethanol solution of 2~6 times the volume of *Piper laetispicum* material, discard the eluent;

Step (4): Then elute with 80%~95% ethanol solution of 4~8 times the volume of *Piper laetispicum* material, collect the eluent, concentrate to brown viscous extract, vacuum dry with the temperature controlled not to exceed 70° C. to obtain said *Piper laetispicum* extract.

Preferably, the preparation method of *Piper laetispicum* extract includes the following steps:

Step (1): After cutting or powdering of the *Piper laetispicum* material, add 90%~95% ethanol solution of 19~21 times the weight of the material to impregnate or percolate to obtain a crude extract;

Step (2): Concentrate the crude extract obtained in step (1) to an alcohol content of 35%~45%, in which the concentrating temperature is controlled not to exceed 70° C.;

Step (3): Load the crude extract concentrated in step (2) onto the D101 macroporous adsorption resin column, and elute in sequence with 40%~50% of 3~5 times the volume of *Piper laetispicum* material and 60%~70% ethanol solution of 2~3 times the volume of *Piper laetispicum* material, discard the eluent;

Step (4): Then elute with 90%~95% ethanol solution of 5~7 times the volume of *Piper laetispicum* material, collect the eluent, concentrate to brown viscous extract, vacuum dry with the temperature controlled not to exceed 70° C. to obtain said *Piper laetispicum* extract.

Most preferably, the preparation method of *Piper laetispicum* extract includes the following steps:

Step (1): After cutting or powdering of the *Piper laetispicum* material, add 95% ethanol solution of 20 times the weight of the material to impregnate or percolate to obtain a crude extract;

Step (2): Concentrate the crude extract obtained in step (1) to an alcohol content of 40%, in which the concentrating temperature is controlled not to exceed 70° C.;

Step (3): Load the crude extract concentrated in step (2) onto the D101 macroporous adsorption resin column, and elute in sequence with 45% of 4 times the volume of *Piper laetispicum* material and 65% ethanol solution of 2 times the volume of *Piper laetispicum* material, discard the eluent;

Step (4): Then elute with 95% ethanol solution of 6 times the volume of *Piper laetispicum* material, collect the eluent, concentrate to brown viscous extract, vacuum dry with the temperature controlled not to exceed 70° C. to obtain said *Piper laetispicum* extract.

Further, said *Piper laetispicum* material in step (1) is the above-ground part, or the above-ground part and the underground part of *Piper laetispicum*.

The third object of the present invention is to provide an application of said *Piper laetispicum* extract as an active ingredient in the preparation of a medicament for preventing, relieving and treating mental diseases or in the preparation of a health product for relieving mental diseases.

Further, the mental diseases include depression, anxiety and so on.

The fourth object of the present invention is to provide a medicament for the prevention, alleviation and treatment of mental diseases, which comprises said *Piper laetispicum* extract.

The fifth object of the present invention is to provide a health product for relieving mental diseases, which comprises said *Piper laetispicum* extract.

Further, the medicament or health product can be prepared into a pharmaceutically acceptable dosage form.

According to the implementation of the above technical solutions, the present invention has the following advantages compared with the prior art:

The present invention improves the preparation method to obtain the *Piper laetispicum* extract, separates and identifies the chemical compounds of the extract to obtain sesamin, (2E,6E)-N-isobutyl-7-(3,4-methylenedioxyphenyl) heptadienamide, N-isobutyldec-trans-2-trans-4-dienamide, (2E, 4E)-N-isobutyl-15-phenylpentadeca-2,4-dienamide, 3',4'-methylenedioxycinnamic acid isobutylamide, 5'-methoxy-3',4'-methylenedioxycinnamic acid isobutylamide, further finds (2E,4E)-N-isobutyldodecane-2,4-dienamide, (2E,4E, 14Z)—N-isobutyleicosane-2,4,14-trienamide from *Piper laetispicum* for the first time, and further finds a new compound (2E,4E)-N-isobutyl-13-phenyltrideca-2,4-dieneamide. The *Piper laetispicum* extract obtained by the preparation method of the present invention has obvious antidepressant effect and good safety.

DETAILED DESCRIPTION OF THE INVENTION

The present invention will be further described in detail below with reference to specific examples, but the present invention is not limited to the following examples. The implementation conditions applied in the examples can be further adjusted according to different requirements of specific use, and the implementation conditions not specified are the conventional conditions in the industry. All other examples obtained by a person of ordinary skill in the art without creative work fall within the protection scope of the present invention.

Example 1

Take the roots and rhizomes of *Piper laetispicum*, crush coarsely, add an appropriate volume of 95% ethanol, impregnate for 24 hours at room temperature, and then add 95% ethanol to 20 times volume to percolate. Concentrate the obtained percolate to an alcohol content of 40%, in which the concentrating temperature is controlled at 60° C., to obtain a concentrated crude *Piper laetispicum* extract. Load the concentrated crude *Piper laetispicum* extract onto a pretreated D101 macroporous adsorption resin, elute in sequence with 4 times volume 40% ethanol and 60% ethanol solution, discard the eluent. And then elute with 6 times volume 95% ethanol, collect the eluent, concentrate to brown viscous extract, vacuum dry with the temperature controlled at 60° C. to obtain the *Piper laetispicum* extract.

The obtained extract is repeatedly subjected to silica gel column chromatography, recrystallization, rapid preparation at medium pressure and high performance liquid preparation chromatography to obtain 9 monomer compounds, which are sequentially numbered as compounds C1, C2, C3, C4, C5, C6, C7, C8 and C9. According to structural identification, except for sesamin the obtained compounds are all amide alkaloids. That is to say, the extract of this example is a composition containing compounds C1, C2, C3, C4, C5, C6, C7, C8 and C9.

I. The Structural Identification of the Compounds of *Piper laetispicum*

According to structural identification, compounds C1-C9 are identified as: 5'-methoxy-3',4'-methylenedioxycinnamic acid isobutylamide (C1); (2E,6E)-N-isobutyl-7-(3,4-methylenedioxyphenyl) heptadienamide (futoamide) (C2); sesamin (C3); N-isobutyldec-trans-2-trans-4-dienamide (pellitorine) (C4); (2E,4E)-N-isobutyldodecane-2,4-dienamide (C5); (2E,4E)-N-isobutyl-13-phenyltrideca-2,4-dienamide (C6); (2E,4E)-N-isobutyl-15-phenylpentadeca-2,4-dienamide (C7); (2E,4E,14Z)—N-isobutyleicosane-2,4,14-trienamide (C8); 3',4'-methylenedioxycinnamic acid isobutylamide (C9).

1. The Structural Identification of Compound C4

White powder, molecular formula: $C_{14}H_{25}NO$. ESI-MS m/z: 224 $[M+1]^+$, 447 [2M+1]+, indicating a molecular weight of 223.

$UV\lambda^{MeOH}_{max}$ nm: 260

$^1$HNMR (400 MHz, CDCl$_3$, δppm): 7.18 (dd, J=15.0, 10.0 Hz, 1H, H-3), 6.13 (dd, J=15.4, 9.8 Hz, 1H, H-4), 6.06 (m, 1H, H-5), 5.76 (d, J=15.0 Hz, 1H, H-2), 5.58 (s, 1H, —NH—), 3.15 (dd, J=12.4, 5.8 Hz, 2H, H-1'), 1.79 (m, 1H, H-2'), 0.92 (d, J=6.7 Hz, 6H, H-3', H-4'), 2.14 (dd, J=13.8, 7.0 Hz, 2H, H-6), 1.41 (m, 2H, H-7), 1.28 (m, 4H, H-8, H-9), 0.89 (t, J=6.9 Hz, 3H, H-10).

$^{13}$CNMR (01 MHz, CDCl$_3$, δppm): 166.40 (C-1), 143.12 (C-3), 141.24 (C-5), 128.22 (C-4), 121.80 (C-2), 46.93 (C-1'), 28.48 (C-2'), 20.11 (C-3', C-4'), 32.89 (C-6), 31.35 (C-8), 28.63 (C-7), 22.45 (C-9), 13.97 (C-10).

In the data of $^1$HNMR (400 MHz, CDCl$_3$): in the low field area, δ7.18 (dd, J=15.0, 10.0 Hz, 1H, H-3) is a signal of 3-position ethylenic proton. Since conjugated with the carbonyl group, it is in the lower field. The J value is 15.0 Hz, indicating it is a trans double bond. δ6.13 (dd, J=15.4, 9.8 Hz, 1H, H-4) and 6.06 (m, 1H, H-5) are 4-position and 5-position signals of ethylenic protons respectively. The J value is 15.4 Hz, which indicating it is a trans double bond. δ5.76 (d, J=15.0 Hz, 1H, H-2) is a signal of 2-position ethylenic proton. The above data speculate that this is a pair of trans-conjugated olefin bond. δ5.58 (s, 1H, —NH—) is an amino signal for amide. In the high field area, δ3.15 (dd, J=12.4, 5.8 Hz, 2H, H-1'), 1.79 (m, 1H, H-2') and 0.92 (d, J=6.7 Hz, 6H, H-3', H-4') are signals of isobutylamine. δ2.14 (dd, J=13.8, 7.0 Hz, 2H, H-6) is a signal of methylene proton linked to a conjugated olefin bond. δ1.41 (m, 2H, H-7) and 1.28 (m, 4H, H-8, H-9) are signals of 3 methylene protons, δ0.89 (t, J=6.9 Hz, 3H, H-10) is a signal of methyl proton, so a —CH$_2$CH$_3$ structure could be inferred to exist.

In the data of $^{13}$CNMR (101 MHz, CDCl$_3$): δ166.40 (C-1) in the low field area is a signal of carbonyl. δ143.12 (C-3), 141.24 (C-5), 128.22 (C-4), 121.80 (C-2) are signals of conjugated double bond. δ46.93 (C-1') in the high field area is a signal of a carbon linked with a nitrogen of an amide, which positions at a lower field, and together with 28.48 (C-2'), 20.11 (C-3, C-4') constitutes signals of carbons in isobutylamine. δ32.89 (C-6) are signals of the carbon linked to a conjugated double bond. δ31.35 (C-8), 28.63 (C-7), 22.45 (C-9) are signals of 3 methylene carbons. 13.97 (C-10) is a signal of a terminal methyl group.

Based on the above analysis, it is confirmed that compound C4 is N-isobutyldec-trans-2-trans-4-dienamide, and its structural formula is:

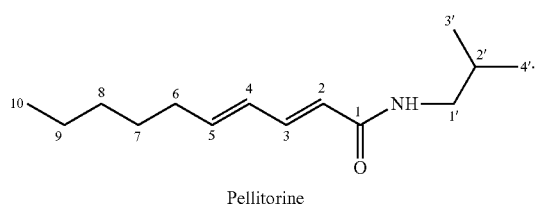 [SMILES: CCCCC/C=C/C=C/C(=O)NCC(C)C]

Pellitorine

2. The Structural Identification of Compound C5

Light yellow powder, molecular formula: $C_{16}H_{29}NO$. ESI-MS m/z: 252 $[M+1]^+$, 503 [2M+1]+, indicating a molecular weight of 251.

$UV\lambda^{MeOH}_{max}$ nm: 261

$^1$HNMR (400 MHz, CDCl$_3$, δppm): 7.18 (dd, J=14.9, 9.9 Hz, 1H, H-3), 6.13 (dd, J=13.9, 8.6 Hz, 1H), 6.05 (dd, J=13.9, 7.6 Hz, 1H, H-5), 5.74 (d, J=15.0 Hz, 1H, H-2), 5.46 (s, 1H, —NH—), 3.16 (t, J=6.5 Hz, 2H, H-1'), 1.80 (m, 1H, H-2'), 0.92 (d, J=6.7 Hz, 6H, H-3', H-4'), 2.14 (dd, J=13.7, 6.9 Hz, 2H, H-6), 1.42 (dd, 2H, H-7), 1.28 (d, J=2.9 Hz, 8H, H-8, H-9, H-10, H-11), 0.88 (t, J=6.8 Hz, 3H, H-12).

In the data of $^1$HNMR (400 MHz, CDCl$_3$): in the low field area, δ7.18 (dd, J=14.9, 9.9 Hz, 1H, H-3) is a signal of 3-position ethylenic proton, since conjugated with a carbonyl group, it is in the lower field. The J value is 14.9 Hz, indicating it is a trans double bond. δ6.13 (dd, J=13.9, 8.6 Hz, 1H) and 6.05 (dd, J=13.9, 7.6 Hz, 1H, H-5) are 4-position and 5-position signals of ethylenic protons respectively. δ5.74 (d, J=15.0 Hz, 1H, H-2) is a signal of 2-position ethylenic proton. 5.46 (s, 1H, —NH—) is an amino signal for amide. In the high field area, 63.16 (t, J=6.5 Hz, 2H, H-1'), 1.80 (m, 1H, H-2') and 0.92 (d, J=6.7 Hz, 6H, H-3', H-4') are signals of isobutylamine. δ2.14 (dd, J=13.7, 6.9 Hz, 2H, H-6) a signal of methylene proton linked to a conjugated olefin bond. δ1.42 (dd, 2H, H-7), 1.28 (d, J=2.9 Hz, 8H, H-8, H-9, H-10, H-11) are signals of methylene protons, 0.88 (t, J=6.8 Hz, 3H, H-12) is a signal of methyl proton, so a —CH$_2$CH$_3$ structure could be inferred to exist.

The spectral characteristics of compound C5 are very similar to compound C4, combined considered with that the molecular weight difference between the two is 28, it can be speculated that the two are homologous, and compound C5 has two more methylene groups than C4.

Based on the above analysis, it is confirmed that compound C5 is (2E,4E)-N-isobutyldodecane-2,4-dienamide, which is found in *Piper laetispicum* for the first time, and its structural formula is:

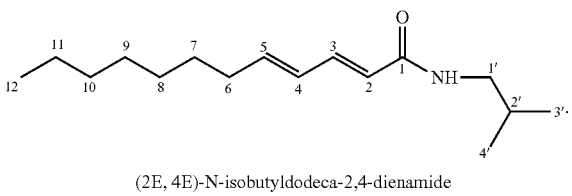 [SMILES: CCCCCCC/C=C/C=C/C(=O)NCC(C)C]

(2E, 4E)-N-isobutyldodeca-2,4-dienamide

3. The Structural Identification of Compound C7

White powder, molecular formula: $C_{25}H_{39}NO$, EI-MS m/z: 370 [M+1]$^+$, 739 [2M+1]$^+$, indicating a molecular weight of 369.

UV$\lambda_{max}^{MeOH}$ nm: 255.

$^1$HNMR (400 MHz, CDCl$_3$, δppm): 7.23 (m, 6H, Ar—H, H-3), 6.08 (qd, J=15.2, 8.2 Hz, 2H, H-4, H-5), 5.75 (d, J=15.0 Hz, 1H, H-2), 5.52 (s, 1H, —NH—), 2.59 (m, 2H, H-15), 1.60 (dd, J=14.6, 7.1 Hz, 2H, H-14), 2.13 (dd, J=13.7, 6.9 Hz, 2H, H-6), 1.39 (dd, J=13.6, 6.9 Hz, 2H, H-7), 1.28 (d, J=15.7 Hz, 12H, H-8H-13), 3.16 (t, J=6.4 Hz, 2H, H-1″), 1.80 (dt, J=13.4, 6.7 Hz, 1H, H-2″), 0.92 (d, J=6.7 Hz, 6H, H-3″, H-4″).

$^{13}$CNMR (101 MHz, CDCl$_3$, δppm): 166.38 (C-1), 143.04 (C-1′), 128.23 (C-3′, C-5′), 128.21 (C-2′, C-6′), 125.54 (C-4′), 142.94 (C-5), 141.26 (C-3), 128.39 (C-4), 121.78 (C-2), 46.93 (C-1″), 28.64 (C-2″), 20.12 (C-3″, C-4″), 35.98 (C-15), 32.94 (C-6), 31.49 (C-14), 29.53 (C-7), 29.48-28.64 (C-8C-13).

In the data of $^1$HNMR (400 MHz, CDCl$_3$): δ7.23 (m, 6H, Ar—H, H-3) is a signal of a monosubstituted benzene ring and a hydrogen in ene. δ6.08 (qd, J=15.2, 8.2 Hz, 2H, H-4, H-5) are 4-position and 5-position signals of ethylenic protons respectively, and the J value is 14.9 Hz, indicating it is a trans double bond. δ5.75 (d, J=15.0 Hz, 1H, H-2) is a signal of 2-position trans ethylenic proton. δ5.52 (s, 1H, —NH—) is an amino signal for amide. δ2.59 (m, 2H, H-15) is a signal of 15-position methylene, since conjugated with a carbonyl group, it is in the lower field. 61.60 (dd, J=14.6, 7.1 Hz, 2H, H-14) a signal of 14-position methylene. δ2.13 (dd, J=13.7, 6.9 Hz, 2H, H-6) is a signal of methylene proton linked to a conjugated olefin bond, and located in the lower field; δ1.39 (dd, J=13.6, 6.9 Hz, 2H, H-7) is a signal of 7-position methylene; δ1.28 (d, J=15.7 Hz, 12H, H-8-H-13) is a signal of 8-position to 13-position methylene; δ3.16 (t, J=6.4 Hz, 2H, H-1″), 1.80 (dt, J=13.4, 6.7 Hz, 1H, H-2″) and 0.92 (d, J=6.7 Hz, 6H, H-3″, H-4″) are signals of isobutylamine.

In the data of $^{13}$CNMR (101 MHz, CDCl$_3$): δ166.38 (C-1) is a signal of carbonyl; δ143.04 (C-1′), 128.23 (C-3′, C-5′), 128.21 (C-2′, C-6′), 125.54 (C-4′) are signals of monosubstituted benzene ring; δ142.94 (C-5), 141.26 (C-3), 128.39 (C-4), 121.78 (C-2) are signals of conjugated double bond signal; δ46.93 (C-1″), 28.64 (C-2″), 20.12 (C-3″, C-4″) are signals of isobutylamine; δ35.98 (C-15) and 32.94 (C-6) are signals of a methylene connecting the benzene ring and the connecting ethylenic bond respectively; δ31.49 (C-14) and 29.53 (C-7) are signals of 14-position and 7-position methylene respectively; δ29.48-28.64 (C-8-C-13) are 6 signals of methylene.

Based on the above analysis, it is confirmed that compound is (2E,4E)-N-isobutyl-15-phenylpentadeca-2,4-dieneamide, and its structural formula is:

4. The Structural Identification of Compound C6

White needle crystal, $C_{23}H_{35}NO$, ESI-MS m/z: 342 [M+1]$^+$, 883 [2M+1]$^+$, indicating a molecular weight of 341.

UV$\lambda_{max}^{MeOH}$ nm: 257

IR: 3305, 2923, 2851, 1657, 1629, 1549, 1465, 1369, 1255, 1160, 998, 746, 696 cm$^{-1}$.

$^1$HNMR (400 MHz, CDCl$_3$, δppm): 7.21 (m, 6H, Ar—H, H-3), 6.08 (m, 2H, H-4, H-5), 5.74 (d, J=15.0 Hz, 1H, H-2), 5.45 (s, 1H, —NH—), 2.59 (m, 2H, H-15), 1.61 (m, 2H, H-14), 2.13 (dd, J=13.7, 6.9 Hz, 2H, H-6), 1.40 (m, 2H, H-7), 1.29 (d, J=7.0 Hz, 8H, H-8-H-11), 3.16 (t, J=6.4 Hz, 2H, H-1″), 1.79 (dt, J=20.2, 6.8 Hz, 1H, H-2″), 0.92 (d, J=6.7 Hz, 6H, H-3″, H-4″)

In the infrared spectrum: strong absorption at 3305 cm$^{-1}$, 1657 cm$^{-1}$, 1549 cm$^{-1}$, and 1255 cm$^{-1}$ indicates that the molecule contains secondary amides, wherein 3305 cm$^{-1}$ is the N—H stretching vibration peak and 1657 cm$^{-1}$ is the C═O stretching vibration peak, 1549 cm$^{-1}$ is N—H in-plane bending vibration, 1255 cm$^{-1}$ is C—N stretching vibration; the strong absorption peaks at 2923 cm$^{-1}$ and 2851 cm$^{-1}$ are caused by —CH$_2$ asymmetric stretching vibration and symmetric stretching vibration; 1629 cm$^{-1}$ is C═C stretching vibration peak, indicating that there are double bonds in the molecule; the absorption peaks at 1465 cm$^{-1}$ and 1369 cm$^{-1}$ are caused by the asymmetric deformation vibration and symmetric bending vibration of —CH$_3$; 1160 cm$^{-1}$ is the C—C skeleton vibration, indicating that the molecule includes —C(CH$_3$)$_2$; 998 cm$^{-1}$ is the C—H out-of-plane bending vibration of ═C—H, and the peak at this point indicates that the molecule contains trans double bonds; 746 cm$^{-1}$ and 696 cm$^{-1}$ are out of the CH plane of the mono-substituted benzene ring bending vibration.

In the data of $^1$HNMR (400 MHz, CDCl$_3$): δ7.21 (m, 6H, Ar—H, H-3) is a signal of mono-substituted benzene ring signal and an ene hydrogen; δ6.08 (m, 2H, H-4, H-5) is a signal of 3-position and 4-position ethylenic proton; δ5.74 (d, J=15.0 Hz, 1H, H-2) is a signal of a proton in 2-position trans-olefin bond; δ5.45 (s, 1H, —NH—) is an amino signal for amide; δ2.59 (m, 2H, H-15) is a signal of 15-position methylene, since conjugated with a carbonyl group, it is in the lower field; δ2.13 (dd, J=13.7, 6.9 Hz, 2H, H-6) is a signal of methylene proton linked to a conjugated olefin bond, and located in the lower field; δ1.40 (m, 2H, H-7) is a signal of 7-position methylene; δ1.29 (d, J=7.0 Hz, 8H, H-8-H-11) is a signal of 8-position to 11-position methylene; δ3.16 (t, J=6.4 Hz, 2H, H-1″), 1.79 (dt, J=20.2, 6.8 Hz, 1H, H-2″) and 0.92 (d, J=6.7 Hz, 6H, H-3″, H-4″) are signals of isobutylamine.

The spectral characteristics of compound C6 are very similar to compound C7, combined considered with that the molecular weight difference between the two is 28, it can be speculated that the two are homologous, and compound C6 is (2E,4E)-N-isobutyl-13-phenyltrideca-2,4-dieneamide. After searching the prior art, as of now, CA has not reported

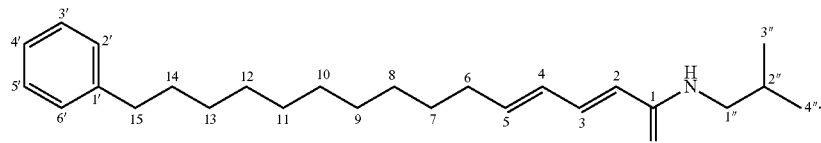

(2E, 4E)-N-isobutyl-15-phenylpentadeca-2,4-dienamide the structure, and the compound is determined to be a new compound of structural formula as C follow:

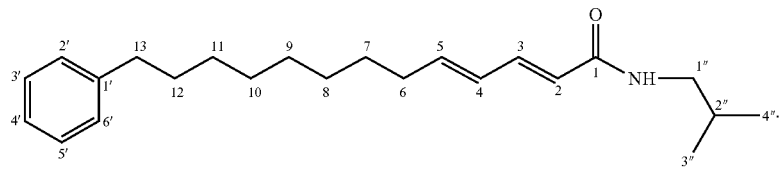

(2E, 4E)-N-isobutyl-13-phenyltrideca-2,4-dienamide

Table 1 is the spectral data of compound C7 and compound C6 $^1$HNMR (400 MHz, CDC$_{l3}$).

TABLE 1

| Position | 1HNMR(δ) | | Multiplicity(J in Hz) | |
| --- | --- | --- | --- | --- |
| | Compound 7 | Compound 6 | Compound 7 | Compound 6 |
| 1 | | | | |
| 2 | 5.75 | 5.74 | D(15) | D(15) |
| 1' | | | | |
| 3 | 7.23 | 7.21 | | |
| 2', 6' | | | | |
| 3', 5' | | | | |
| 4' | | | | |
| 4 | 6.08 | 6.08 | qd(15.2, 8.2) | |
| 5 | | | | |
| 6 | 2.13 | 2.13 | dd(13.7, 6.9) | dd(13.7, 6.9) |
| 7 | 1.39 | 1.4 | dd(13.6, 6.9) | |
| 8~13(11) | 1.28 | 1.29 | d(15.7) | d(7) |
| 14(12) | 1.6 | 1.61 | dd(14.6, 7.1) | |
| 15(13) | 2.59 | 2.59 | | |
| 1" | 3.16 | 3.16 | t(6.4) | t(6.4) |
| 2" | 1.8 | 1.79 | dt(13.4, 6.7) | dt(20.2, 6.8) |
| 3", 4", | 0.92 | 0.92 | d(6.7) | d(6.7) |
| NH | 5.52 | 5.45 | | |

5. The Structural Identification of Compound C8

White powder, $C_{24}H_{43}NO$, ESI-MS m/z: 362 [M+1]$^+$, 723 [2M+1]$^+$, indicating a molecular weight of 361.

UV$\lambda^{MeOH}_{max}$ nm: 260.

$^1$HNMR (400 MHz, CDCl$_3$, δppm): 7.20 (m, 1H, H-3), 6.12 (m, 1H, H-4), 6.05 (dd, J=14.9, 6.4 Hz, 1H, H-5), 5.75 (d, J=15.0 Hz, 1H, H-2), 5.51 (s, 1H, —NH—), 5.35 (t, J=6.0 Hz, 2H), 3.16 (t, J=6.1 Hz, 2H, H-1'), 1.80 (dt, J=13.1, 6.5 Hz, 1H, H-2'), 0.93 (m, 6H, H-3', H-4'), 2.14 (d, J=6.6 Hz, 2H, H-6), 2.02 (s, 4H), 1.41 (s, 2H, H-7), 1.27 (s, 16H), 0.93 (m, 3H, H-20).

$^{13}$CNMR (101 MHz, CDCl$_3$, δppm): 166.36 (C-1), 143.14 (C-3), 141.26 (C-5), 128.12 (C-4), 121.88 (C-2), 129.74, 46.93 (C-1'), 28.81 (C-2'), 20.11 (C-3', C-4'), 32.94 (C-6), 14.08 (C-20).

In the data of $^1$HNMR (400 MHz, CDCl$_3$): δ 7.20 (m, 1H, H-3) is a signal of 3-position ethylenic proton, since conjugated with a carbonyl group, it is in the lower field. The J value is 14.9 Hz; δ6.12 (m, 1H, H-4) and 6.05 (dd, J=14.9, 6.4 Hz, 1H, H-5) are 4-position and 5-position signals of ethylenic protons respectively. The J value is 14.9 Hz, indicating it is a trans double bond. δ5.75 (d, J=15.0 Hz, 1H, H-2) is a signal of 2-position ethylenic proton. The J value is 15 Hz, indicating it is a trans double bond. The above data speculate that this is a pair of trans-conjugated olefin bonds. δ5.51 (s, 1H, —NH—) is an amino signal for amide; δ5.35 (t, J=6.0 Hz, 2H) is a signal of an ethylenic proton. The J value is 14.9 Hz, indicating a cis double bond. There is no benzene ring proton signal in the low field region. In the high field area, δ3.16 (t, J=6.1 Hz, 2H, H-1'), 1.80 (dt, J=13.1, 6.5 Hz, 1H, H-2') and 0.93 (m, 6H, H-3', H-4') are signals of isobutylamine; δ2.14 (d, J=6.6 Hz, 2H, H-6) is a signal of a methylene proton connected to a conjugated olefin bond; δ2.02 (s, 4H) is a signal of methylene protons at both ends of the ethylenic bond; δ1.41 (s, 2H, H-7) and 1.27 (s, 16H) are signals of 9 methylene protons; δ0.93 (m, 3H, H-20) is a signal of methyl proton, which can be inferred to have —CH$_2$CH$_3$ structure.

In the data of $^{13}$CNMR (101 MHz, CDCl$_3$): δ 166.36 (C-1) is a carbonyl signal; δ143.14 (C-3), 141.26 (C-5), 128.12 (C-4), 121.88 (C-2) are signals of a conjugated double bond; δ129.74 is a signal of isolated double bond; δ46.93 (C-1') is a signal of a carbon linked with a nitrogen of an amide, which positions at a lower field, and together with δ28.81 (C-2'), 20.11 (C-3', C-4') constitutes signals of carbons in isobutylamine; δ32.94 (C-6) is a signal of a carbon connected to the conjugated double bond; δ31.88-28.90 and δ22.33 are signals of 9 methylene carbons; δ27.19 and 26.91 are signals of methylene carbons at both ends of the isolated double bond; δ14.08 (C-20) is a signal of a terminal methyl group.

Based on the above analysis, it is confirmed that compound is (2E,4E,14Z)—N-isobutyleicosane-2,4,14-trienamide, which is found in *Piper laetispicum* for the first time, and its structural formula is:

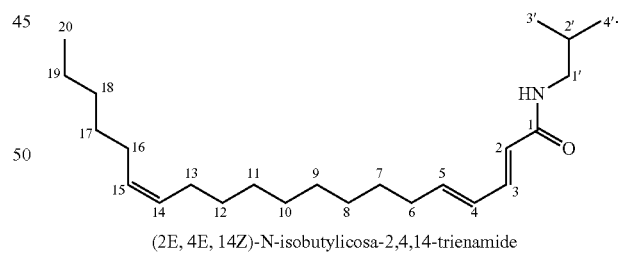

(2E, 4E, 14Z)-N-isobutylicosa-2,4,14-trienamide

6. The Structural Identification of Compound C3

White needle crystal, molecular formula: $C_{20}H_{18}O_6$, ESI-MS m/z: 337 [M+1−18]+, 709 [2M+1]+, indicating a molecular weight of 354.

UV$\lambda^{MeoH}_{max}$ nm: 236, 286

$^1$HNMR (400 MHz, CDCl$_3$, δppm): 6.84 (s, 2H, H-2, H-2'), 6.79 (m, 4H, H-5, H-5', H-6, H-6'), 5.94 (s, 4H, H-10, H-10'), 4.71 (d, J=4.1 Hz, 2H, H-7, H-7'), 4.23 (dd, J=9.0, 6.8 Hz, 2H, H-9a, H-9α'), 3.87 (dd, J=9.2, 3.4 Hz, 2H, H-9O, H-9O'), 3.04 (m, 2H, H-8, H-8').

$^{13}$CNMR (101 MHz, CDCl$_3$, δppm): 147.99 (C-4, C-4'), 147.13 (C-3, C-3'), 135.11 (C-1, C-1'), 119.34 (C-6, C-6'), 108.19 (C-5, C-5'), 106.50 (C-2, C-2'), 101.07 (C-10, C-10'), 85.81 (C-7, C-7'), 71.73 (C-9, C-9'), 54.36 (C-8, C-8')

In the data of $^1$HNMR (400 MHz, CDCl$_3$): δ6.84 (s, 2H, H-2, H-2') and 6.79 (m, 4H, H-5, H-5', H-6, H-6') are signals of protons of trisubstituted benzene ring fragments; δ5.94 (s, 4H, H-10, H-10') are signals of protons of methylenedioxy; δ4.71 (d, J=4.1 Hz, 2H, H-7, H-7'), 4.23 (dd, J=9.0, 6.8 Hz, 2H, H-9α, H-9α'), 3.87 (dd, J=9.2, 3.4 Hz, 2H, H-9β, H-9β'), 3.04 (m, 2H, H-8, H-8') are signals of protons of tetrahydrofuran.

In the data of $^{13}$CNMR (101 MHz, CDCl$_3$), there are 10 signals of carbons, wherein: δ147.99 (C-4, C-4'), 147.13 (C-3, C-3'), 135.11 (C-1, C-1') are signals of quaternary carbons on the benzene ring; δ119.34 (C-6, C-6'), 108.19 (C-5, C-5'), 106.50 (C-2, C-2') are signals of tertiary carbons on benzene ring; δ101.07 (C-10, C-10') is a signal of methylenedioxy carbon; δ85.81 (C-7, C-7'), 71.73 (C-9, C-9'), 54.36 (C-8, C-8') are signals of carbon s of tetrahydrofuran.

Based on the above analysis, it is confirmed that compound C4 is Sesamin, and its structural formula is:

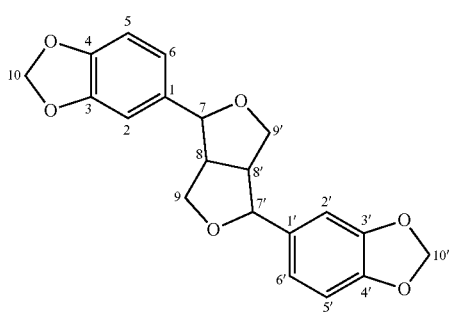

7. The Structural Identification of Compound C1

White needle crystal, the molecular formula is $C_{15}H_{19}NO_4$, EI-MS m/z: 277 [M]$^+$, indicating a molecular weight of 277.

$^1$HNMR (400 MHz, CDCl$_3$, δppm): 0.95 (6H, d, J=6.6 Hz, —(CH$_3$)$_2$); 1.85 (1H, m, —CH(CH$_3$)$_2$); 3.22 (2H, dd, J$_1$=J$_2$=6.6 Hz, —CH$_2$CH(CH$_3$)$_2$); 3.89 (3H, s, Ar—OCH$_3$); 6.02 (2H, s, Ar—OCH$_2$O); 6.31 (1H, d, J=15.6 Hz); 6.66 (1H, d, J=1.2); 6.71 (1H, d, J=1.2 Hz); 7.52 (1H, d, J=15.6 Hz).

$^{13}$CNMR (101 MHz, CDCl$_3$, δppm): 166.07, 149.22, 143.58, 140.79, 136.70, 129.66, 119.22, 108.92, 101.80, 100.79, 56.54, 47.13, 28.59, 20.12.

Based on analysis, compound C1 is 5'-methoxy-3',4'-methylenedioxycinnamic acid isobutylamide, and its structural formula is:

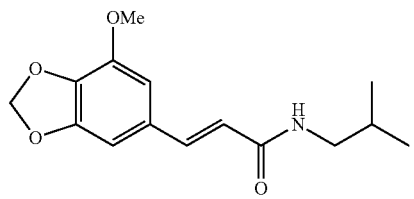 [SMILES: COc1cc(/C=C/C(=O)NCC(C)C)cc2c1OCO2]

8. The Structural Identification of Compound C2

Colorless crystals, the molecular formula is C is H$_{23}$NO$_3$, EI-MS m/z: 301 [M]$^+$, indicating a molecular weight of 301.

$^1$HNMR (400 MHz, CDCl$_3$, δppm): 0.93 (6H, d, J=6.6 Hz, —CH(CH$_3$)$_2$); 1.81 (1H, m, —CH(CH$_3$)$_2$); 2.43 (2H, dd, J=6.6 Hz); 2.67 (2H, dd, J=3.6 Hz, 7.2 Hz); 3.18 (2H, t, J=6.0 Hz, —NH—CH$_2$—); 5.59 (1H, br, —NH—); 5.77 (1H, d, J=13.8 Hz); 5.92 (2H, s, Ar—OCH$_2$O); 6.09 (2H, m); 6.61 (1H, dd, J=1.2 Hz, 2.4 Hz); 6.67 (1H, dd, J=0.6 Hz); 6.74 (1H, dd, J=3.6 Hz); 7.27 (1H, m).

$^{13}$CNMR (101 MHz, CDCl$_3$, δppm): 166.47, 147.61, 145.77, 141.78, 141.30, 135.07, 128.86, 121.99, 121.17, 108.81, 108.17, 100.79, 47.05, 34.95, 28.60, 20.11, 19.87.

Based on analysis, compound C2 is (2E,6E)-N-isobutyl-7-(3,4-methylenedioxyphenyl) heptadienamide (Futoamide), and its structural formula is:

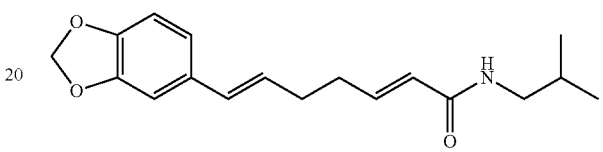

9. The Structural Identification of Compound C9

Colorless crystals, the molecular formula is $C_{14}H_{17}NO_3$, EI-MS m/z: 247 [M]$^+$, indicating a molecular weight of 247.

$^1$HNMR (400 MHz, CDCl$_3$, δppm): 0.96 (6H, d, J=6.60 Hz, —CH(CH3)2); 1.85 (1H, m, —CH(CH3)2); 3.23 (2H, dd, J$_1$=J$_2$=5.49 Hz, —NH—CH2-); 5.64 (1H, bd, —NH—); 6.00 (2H, s, Ar—OCH2O); 6.25 (1H, d, J=15.38 Hz); 6.81 (1H, d, J=7.69 Hz); 7.00 (2H, d, J=9.34 Hz); 7.56 (1H, d, J=15.38 Hz).

$^{13}$CNMR (101 MHz, CDCl$_3$, δ ppm): 66.52, 149.43, 148.64, 141.15, 129.69, 124.32, 119.18, 108.99, 106.73, 101.90, 47.50, 29.12, 20.64.

Based on analysis, compound C9 is 3',4'-methylenedioxycinnamic acid isobutylamide, and its structural formula is:

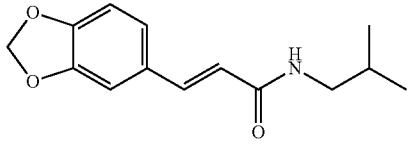 [SMILES: CC(C)CNC(=O)/C=C/c1ccc2c(c1)OCO2]

II. Research on the Determination Method of Amide Alkaloids in *Piper laetispicum* Extract (HPLC Content Determination Method)

(1) Instruments, Reagents, Controls

Instruments: Agilent 1100 high-performance liquid chromatograph, Chemstation Edition chromatographic workstation.

Reagents: methanol (chromatographically pure), acetonitrile (chromatographically pure), purified water (Wahaha).

Reference substance: all the separated compound monomers obtained above are purified by recrystallization, rapid preparation of medium pressure or high performance liquid preparation chromatography and other methods, to obtain reference substances for content determination. According to the chromatographic conditions of the present method, the normalized purity is over 98%, which meet the relevant requirements.

(2) Chromatographic Conditions

Agilent 1100 high performance liquid chromatograph, Chemstation Edition chromatographic workstation; column: BISCHOFF Prontosil 120-5-C18-SH; mobile phase: methanol-acetonitrile-water; flow rate: 1 ml/min; column temperature: 40° C.; detector: DAD detector; detection wavelength: 240 nm; injection volume: 10 μl; gradient elution procedures are shown in Table 2.

TABLE 2

| Time(min) | methanol(%) | acetonitrile (%) | water (%) |
|---|---|---|---|
| 0 | 10 | 0 | 90 |
| 30 | 50 | 50 | 0 |
| 35 | 50 | 50 | 0 |
| 45 | 10 | 0 | 90 |

(3) Preparation of Sample Solution

Take 40 mg of *Piper laetispicum* extract, weigh accurately, put in a 50 ml brown volumetric flask, add methanol until near scale, place the volumetric flask in an ultrasonic cleaner to ultrasonically dissolve, remove and let it cool down, add methanol to the scale, shake well, filter with a micropore filter membrane, then the sample solution is obtained. Placed the sample solution in a dark container.

(4) Determination Methods

Accurately absorb 10 μl each of the sample solution and the reference solution, and inject into a high-performance liquid chromatograph, record the peak area of the chromatogram, and calculate the content according the external standard method. According the determination the extract includes: sesamin; (2E,6E)-N-isobutyl-7-(3,4-methylenedioxyphenyl) heptadienamide; (2E,4E)-N-isobutyldodecane-2,4-dieneamide; (2E,4E)-N-isobutyl-15-phenylpentadeca-2,4-dieneamide; (2E,4E,14Z)—N-isobutyleicosane-2,4,14-trienamide; (2E,4E)-N-isobutyl-13-phenyltrideca-2,4-dieneamide; 5'-methoxy-3',4'-methylenedioxy cinnamic acid isobutylamide; 3',4'-methylenedioxycinnamic acid isobutylamide; N-isobutyldec-trans-2-trans-4-dienamide. The total alkaloid content is 70.15%.

Example 2

Take the roots and rhizomes of *Piper laetispicum*, crush coarsely, add an appropriate volume of 95% ethanol, impregnate for 24 hours at room temperature, and then add 95% ethanol to 20 times volume to percolate. Concentrate the obtained percolate to an alcohol content of 40%, in which the concentrating temperature is controlled at 60° C., to obtain a concentrated crude *Piper laetispicum* extract. Load the concentrated crude *Piper laetispicum* extract onto a pretreated D101 macroporous adsorption resin, elute in sequence with 4 times volume 45% ethanol and 2 times volume 65% ethanol solution, discard the eluent. And then elute with 6 times volume 95% ethanol, collect the eluent, concentrate to brown viscous extract, vacuum dry with the temperature controlled at 60° C. to obtain the *Piper laetispicum* extract. The yield of the extract is 1.21%. According the HPLC content determination, the extract of the present example includes: sesamin; (2E,6E)-N-isobutyl-7-(3,4-methylenedioxyphenyl) heptadienamide; (2E,4E)-N-isobutyldodecane-2,4-dieneamide; (2E,4E)-N-isobutyl-15-phenylpentadeca-2,4-dieneamide; (2E,4E,14Z)—N-isobutyleicosane-2,4,14-trienamide; (2E,4E)-N-isobutyl-13-phenyltrideca-2,4-dieneamide; 3',4'-methylenedioxycinnamic acid isobutylamide; N-isobutyldec-trans-2-trans-4-dienamide. The total alkaloid content is 75.39%. That is, the extract of this example is a composition containing compounds C2, C3, C4, C5, C6, C7, C8, and C9.

Example 3

Take the roots and rhizomes of *Piper laetispicum*, crush coarsely, add an appropriate volume of 95% ethanol, impregnate for 24 hours at room temperature, and then add 95% ethanol to 25 times volume to percolate. Concentrate the obtained percolate to an alcohol content of 45%, in which the concentrating temperature is controlled at 60° C., to obtain a concentrated crude *Piper laetispicum* extract. Load the concentrated crude *Piper laetispicum* extract onto a pretreated D101 macroporous adsorption resin, elute in sequence with 4 times volume 50% ethanol and 4 times volume 70% ethanol solution, discard the eluent. And then elute with 6 times volume 95% ethanol, collect the eluent, concentrate to viscous extract, vacuum dry with the temperature controlled at 60° C. to obtain the *Piper laetispicum* extract. The yield of the extract is 0.81%. According the HPLC content determination, the extract of the present example includes: (2E,4E)-N-isobutyldodecane-2,4-dieneamide; (2E,4E)-N-isobutyl-15-phenylpentadeca-2,4-dieneamide; (2E,4E,14Z)—N-isobutyleicosane-2,4,14-trienamide; (2E,4E)-N-isobutyl-13-phenyltrideca-2,4-dieneamide; N-isobutyldec-trans-2-trans-4-dienamide. The total alkaloid content is 35.25%. That is, the extract of this example is a composition containing compounds C4, C5, C6, C7 and C8.

Example 4

Take the roots and rhizomes of *Piper laetispicum*, crush coarsely, add an appropriate volume of 90% ethanol, impregnate for 24 hours at room temperature, and then add 95% ethanol to 15 times volume to percolate. Concentrate the obtained percolate to an alcohol content of 35%, in which the concentrating temperature is controlled at 60° C., to obtain a concentrated crude *Piper laetispicum* extract. Load the concentrated crude *Piper laetispicum* extract onto a pretreated D101 macroporous adsorption resin, elute in sequence with 2 times volume 40% ethanol and 2 times volume 60% ethanol solution, discard the eluent. And then elute with 6 times volume 90% ethanol, collect the eluent, concentrate to viscous extract, vacuum dry with the temperature controlled at 60° C. to obtain the *Piper laetispicum* extract. The yield of the extract is 1.42%. According the HPLC content determination, the extract of the present example includes: sesamin; (2E,6E)-N-isobutyl-7-(3,4-methylenedioxyphenyl) heptadienamide; (2E,4E)-N-isobutyldodecane-2,4-dieneamide; (2E,4E)-N-isobutyl-15-phenylpentadeca-2,4-dieneamide; (2E,4E,14Z)—N-isobutyleicosane-2,4,14-trienamide; (2E,4E)-N-isobutyl-13-phenyltrideca-2,4-dieneamide; 5'-methoxy-3',4'-methylenedioxycinnamic acid isobutylamide; 3',4'-methylenedioxycinnamic acid isobutylamide; N-isobutyldec-trans-2-trans-4-dienamide. The total alkaloid content is 55.23%. That is, the extract of this example is a composition containing compounds C1, C2, C3, C4, C5, C6, C7, C8 and C9.

Comparative Example 1

Take the roots and rhizomes of *Piper laetispicum*, crush coarsely, add an appropriate volume of 50% ethanol, impregnate for 24 hours at room temperature, and then add 50% ethanol to 20 times volume to percolate. Concentrate the obtained percolate to an alcohol content of 30%, in which the concentrating temperature is controlled at 60° C., to obtain a concentrated crude *Piper laetispicum* extract. Load the concentrated crude *Piper laetispicum* extract onto a pretreated D101 macroporous adsorption resin, elute with 4 times volume 30% ethanol, discard the eluent. And then elute with 6 times volume 70% ethanol, collect the eluent, concentrate to viscous extract, vacuum dry with the temperature controlled at 60° C. to obtain an extract.

Comparative Example 2

Take the roots and rhizomes of *Piper laetispicum*, crush coarsely, add an appropriate volume of 70% ethanol, impregnate for 24 hours at room temperature, and then add 70% ethanol to 20 times volume to percolate. Concentrate the obtained percolate to an alcohol content of 30%, in which the concentrating temperature is controlled at 60° C., to obtain a concentrated crude *Piper laetispicum* extract. Load the concentrated crude *Piper laetispicum* extract onto a pretreated D101 macroporous adsorption resin, elute with 4 times volume 40% ethanol, discard the eluent. And then elute with 6 times volume 85% ethanol, collect the eluent, concentrate to viscous extract, vacuum dry with the temperature controlled at 60° C. to obtain an extract.

Comparative Example 3 (ZL200410084791.7)

Take the roots and rhizomes of *Piper laetispicum*, cut into segments, add an appropriate volume of 80% ethanol, impregnate for 24 hours at room temperature, and then add ethanol of the same concentration to 15 times volume to percolate. Add 60° C. water of the same volume to the percolate and stir to mix, then load the diluted percolate onto the D101 macroporous adsorption resin column. After flowing through, elute with 50% and 85% ethanol successively. Collect the liquid eluted by 85% ethanol, concentrate and dry at a temperature not exceeding 70° C. to obtain a refined extract. According to HPLC determination, the refined extract includes: 5'-methoxy-3',4'-methylenedioxycinnamic acid-tetrahydropyrrole; 3',4'-methylenedioxycinnamic acid-isobutylamide; 5'-methoxy-3',4'-methylenedioxycinnamic acid isobutylamide; N-isobutyldec-trans-2-trans-4-dienamide; 1-[(2E,4E)-2,4-decadienoyl]pyrrolidine; N-isobutyl-9-(3',4'-methylenedioxyphenyl)-2E,8E-nonadienamide; 1-[(2E)-5-(3,4-Methylenedioxyphenyl)]tetrahydropyrrole.

Comparative Example 4 (PCT/CN2005/002034)

Take the dry roots and rhizomes of *Piper laetispicum* 1 Kg, cut into segments, add an appropriate volume of 90% ethanol, impregnate for 48 hours at room temperature, and then add 20 L ethanol of the same concentration to percolate. Add 15 L warm water to the percolate and stir to mix, then load the diluted percolate onto the D101 macroporous adsorption resin column. After flowing through, elute with 40% and 90% ethanol successively. Collect the liquid eluted by 90% ethanol, concentrate and dry at a temperature not exceeding 70° C. to obtain a refined extract. The refined extract includes: 5'-methoxy-3',4'-methylenedioxycinnamic acid tetrahydropyrrole; 3',4'-methylenedioxycinnamic acid isobutylamide; 5'-methoxy-3',4'-methylenedioxycinnamic acid isobutylamide; N-isobutyldec-trans-2-trans-4-dienamide; 1-[(2E,4E)-2,4-decadienoyl]pyrrolidine; N-isobutyl-9-(3',4'-methylenedioxyphenyl)-2E,8E-nonadienamide; 4,5-dihydroepiperminine, and piperamide.

Comparative Example 5 (201010296974.0)

Take the roots and rhizomes of *Piper laetispicum*, crush coarsely, add 10 times volume of 70% ethanol, impregnate at room temperature to obtain a crude extract solution, and then concentrate the crude extract solution under vacuum to about 25% of the original volume. Load the concentrated crude extract onto a non-polar macroporous adsorption resin column, elute in sequence with 30% ethanol and 80% ethanol, collect the eluent eluted by 80% ethanol, concentrate and dry to obtain a refined extract.

The following tests were carried out on the *Piper laetispicum* extracts in Examples 1-4 and Comparative Examples 1-5:

1. Mouse Tail Hanging Test

Kunming mice (male, 18-20 g) were randomly divided into 14 groups, each with 10 rats. Each group was given the corresponding dose of extract as shown in Table 3, and normal saline was used as control. The positive control group was venlafaxine. Continuous administered for 14 days, one time per day. One hour after the last oral administration, the mouse tail hanging test was carried out. The tails of the mice were glued on a wooden bar 50 cm above the table top to make them stand upside down, and the mouse sight was isolated using plates around. The mice would struggle to overcome the abnormal posture, but appear immobile after a period of activity, showing state of despair Duration was 6 minutes, the time of immobility within 6 minutes was recorded.

TABLE 3

Results of Mouse tail hanging test (n = 10, $\bar{x} \pm SD$)

| Group | Dosage of administration (mg/kg/d) | Immobility time within 6 min(s) |
|---|---|---|
| Control | — | 158.6 ± 53.8 |
| Venlafaxine | 50 | 60.9 ± 38.5** |
| Extract of Example 1 | 20 | 62.5 ± 25.6** |
| Extract of Example 1 | 10 | 73.8 ± 30.2** |
| Extract of Example 1 | 5.0 | 82.4 ± 23.4* |
| Extract of Example 1 | 2.5 | 95.3 ± 33.6* |
| Extract of Example 2 | 20 | 61.1 ± 39.8** |
| Extract of Example 2 | 10 | 70.4 ± 26.4** |
| Extract of Example 2 | 5.0 | 80.9 ± 21.8* |
| Extract of Example 2 | 2.5 | 90.4 ± 32.5* |
| Extract of Example 3 | 20 | 70.6 ± 20.6** |
| Extract of Example 4 | 20 | 65.3 ± 18.7** |
| Extract of Comparative Example 4 | 20 | 78.1 ± 28.4* |
| Extract of Comparative Example 4 | 10 | 82.9 ± 34.3* |
| Extract of Comparative Example 4 | 5.0 | 92.5 ± 48.2* |
| Extract of Comparative Example 4 | 2.5 | 108.9 ± 32.7 |
| Extract of Comparative Example 3 | 20 | 80.2 ± 31.6* |
| Extract of Comparative Example 1 | 20 | 95.8 ± 28.6* |
| Extract of Comparative Example 2 | 20 | 93.4 ± 29.3* |
| Extract of Comparative Example 5 | 20 | 98.3 ± 30.2* |

**$P < 0.01$ *$P < 0.05$ Compared with Group Control

From the results in Table 3, it can be seen that the oral administration of 20, 10, 5 and 2.5 mg/kg/d of the extract of the present invention (extracts of Examples 1-4) in mice for two weeks significantly shortened the immobile time. Compared with the control group, P values are all less than 0.05. At 10 mg/kg/d, P value is less than 0.01. And at 2.5 mg/kg/d, the present invention extract shows good antidepressant effect.

It is found by comparison that when the dosage is 5 mg/kg/d the biological activity of the extracts of the present invention is equivalent to that of the extract of Comparative Example 4 at 20 mg/kg/d, indicating that the biological activity of the *Piper laetispicum* extract of the present invention is significantly higher than that of Comparative Example 4, and also better than other extracts of prior art.

2. Mouse Swimming Test

Kunming mice (male, 18-20 g) were randomly divided into 12 groups, each with 10 rats. Each group was given the corresponding dose of extract as shown in Table 4 and normal saline was used as control. The positive control group was venlafaxine. Continuous administered for 14 days, one time per day. One hour after the last oral administration, the mice were placed into a glass tank of 10×20 cm and water depth of 10 cm (water temperature 25° C.) for a swimming test. The swimming duration was 6 minutes, the time to stop motion within 5 minutes was recorded.

TABLE 4

Results of Mouse swimming test ((n=10, x̄ ± SD)

| Group | Dosage of administration (mg/kg/d) | Stop motion within 5 min (s) |
|---|---|---|
| Control | — | 125.6 ± 18.6 |
| Venlafaxine | 50 | 75.8 ± 19.4** |
| Extract of Example 1 | 10 | 70.4 ± 12.1** |
| Extract of Example 1 | 5.0 | 83.3 ± 14.6** |
| Extract of Example 1 | 2.5 | 87.8 ± 15.3** |
| Extract of Example 2 | 10 | 70.9 ± 13.5** |
| Extract of Example 2 | 5.0 | 79.6 ± 16.3** |
| Extract of Example 2 | 2.5 | 83.5 ± 17.8** |
| Extract of Example 3 | 10 | 80.5 ± 11.2** |
| Extract of Example 4 | 10 | 75.2 ± 12.7** |
| Extract of Comparative Example 4 | 10 | 85.1 ± 13.2** |
| Extract of Comparative Example 4 | 5.0 | 92.3 ± 15.6** |
| Extract of Comparative Example 4 | 2.5 | 109.2 ± 27.5 |
| Extract of Comparative Example 3 | 10 | 87.5 ± 22.7** |
| Extract of Comparative Example 1 | 10 | 99.4 ± 18.3* |
| Extract of Comparative Example 2 | 10 | 98.3 ± 25.9* |
| Extract of Comparative Example 5 | 10 | 101. ± 10.7* |

**P < 0.01 *P < 0.05 Compared with Group Control

It can be seen from the results in Table 4 that the oral administration of 10, 5, 2.5 mg/kg/d of the extract of the present invention (Extracts of Examples 1-4) in mice for two weeks significantly shortened the time for mice to stop moving. Compared with the control group, the P value is less than 0.05. The extract of the present invention shows good antidepressant effect at 2.5 mg/kg/d.

It is found by comparison that when the dosage is 2.5 mg/kg/d the activity of the extract of Comparative Example 4 shows no significant difference compared with the blank control. Meanwhile the biological activity of the extract of the present invention is equivalent to the biological activity of the extract of Comparative Example 4 at 10.0 mg/kg/d, indicating that the biological activity of the *Piper laetispicum* extract of the present invention is significantly higher than that of Comparative Example 4, and also better than other extracts of prior art.

3. Rat Learned Helplessness Test

Wistar rats were selected and randomly grouped into 10 rats in each group. The learned helplessness test model was used in which the corresponding dose of extracts shown as in Table 5 were administered orally by gavage. The positive control was venlafaxine. Continuous administered for 7 days, one time per day. 24 h after the last oral administration, a conditional avoidance test is implemented.

TABLE 5

Results of Rat learned helplessness test ((u test: n = 300, x̄ ± SD)

| Group | Dosage of administration (mg/kg/d) | Escape latency (s) |
|---|---|---|
| Blank Control | — | 9.53 ± 11.26 |
| Model control | — | 21.23 ± 12.06## |
| Venlafaxine | 30 | 14.15 ± 12.32** |

TABLE 5-continued

Results of Rat learned helplessness test ((u test: n = 300, x̄ ± SD)

| Group | Dosage of administration (mg/kg/d) | Escape latency (s) |
|---|---|---|
| Extract of Example 2 | 10 | 12.86 ± 13.64** |
| Extract of Example 2 | 5.0 | 14.52 ± 13.45** |
| Extract of Example 2 | 2.5 | 15.83 ± 11.98** |
| Extract of Example 2 | 1.25 | 19.32 ± 12.01 |
| Extract of Comparative Example 4 | 10 | 15.32 ± 12.63** |
| Extract of Comparative Example 4 | 5.0 | 17.56 ± 13.24* |
| Extract of Comparative Example 4 | 2.5 | 19.76 ± 12.36 |
| Extract of Comparative Example 4 | 1.25 | 20.13 ± 11.25 |

: P < 0.01 Compared with Group Blank Control
**: P < 0.01 Compared with Group Model Control
*: P < 0.05 Compared with Group Model Control The learned helpless model is an effective animal model of depression. Table 5 shows that the average escape latency of the model group animals is significantly longer than that of the Blank Control group (P<0.01), the animals show a clear state of despair, indicating that the modelling is success. At the doses of 10, 5, 2.5 mg/kg/d, the positive control drug venlafaxine and the extract of the present invention (Extract of Example 2) significantly shortened the escape latency of the rats, and compared with the model control group P<0.01, showing a good antidepressant effect.

It was found by comparison that at the dose was 2.5 mg/mg/d, the extract of Comparative Example 4 did not significantly shorten the escape latency of the rats, indicating that the antidepressant activity of the extract of the present invention is superior to the antidepressant activity of the extract of Comparative Example 4.

4. Light and Dark Box Test in Mice

The mice were randomly divided into groups of 10, and the corresponding doses of extracts were administered as shown in Table 6, in which normal saline was used as control. The positive control drug was diazepam. 60 minutes after oral administration, the light and dark box test was implemented. Each mouse is tested for 5 minutes, and each residence time in the light box and the number of shuttles between the light and dark boxes are recorded.

TABLE 6

Results of Light and dark box test in mice (n = 10, x̄ ± SD)

| Group | Dosage of administration (mg/kg) | Number of shuttles | Time |
|---|---|---|---|
| Control | — | 8.54 ± 0.32 | 73.92 ± 4.95 |
| Diazepam | 2.0 | 14.23 ± 1.06** | 121.23 ± 8.12** |
| Extract of Example 1 | 20 | 12.03 ± 0.87** | 117.73 ± 9.29** |
| Extract of Example 1 | 10 | 10.86 ± 1.36* | 102.25 ± 8.75* |
| Extract of Example 1 | 5 | 7.53 ± 0.55 | 73.14 ± 8.33 |
| Extract of Example 2 | 20 | 12.12 ± 0.98** | 120.86 ± 9.64** |
| Extract of Example 2 | 10 | 11.09 ± 1.43* | 104.25 ± 9.45* |
| Extract of Example 2 | 5 | 8.03 ± 0.45 | 75.84 ± 8.98 |
| Extract of Example 3 | 20 | 11.76 ± 0.66** | 110.42 ± 8.31** |
| Extract of Example 4 | 20 | 19.92 ± 0.54** | 115.37 ± 7.63** |
| Extract of Comparative Example 4 | 20 | 10.98 ± 1.03* | 105.21 ± 8.36* |
| Extract of Comparative Example 4 | 10 | 9.35 ± 0.74 | 80.91 ± 9.24 |
| Extract of Comparative Example 3 | 10 | 8.21 ± 0.62 | 79.76 ± 5.36 |
| Extract of Comparative Example 1 | 20 | 9.12 ± 1.26 | 83.23 ± 7.89 |

**: P < 0.01 Compared with Group Control
*: P < 0.05 Compared with Group Control As shown in Table 6, compared with the group Control, the extract of the present invention at dose 10 mg/kg can significantly increase the entering number and active time in the light box of mice. At the dose 10 mg/kg, P<0.05, and at the dose 20 mg/kg, P<0.01, indicating that the extract of the present invention has an anxiolytic effect. At the same time, it could be found by comparison that that the anti-anxiety effect of the extract of the present invention is better than the extracts of comparative examples.

5. Safety Evaluation of the *Piper laetispicum* Extract-Acute Toxicity Test in Mice Kunming mice (half male and female, weight 18-22 g) were randomly divided into groups of 10, and half male and female in each group. After 4 hours of fasting (with free drinking) for all mice, each group was administered according to the results of the pre-experiment. The administration volume is 0.2 ml/10 g, oral administration. Then observe the reaction after administration of the mice once a day for 14 consecutive days, record the death happening. After the 14-day observation period, the surviving animals were weighed and dissected to observe whether the organs are abnormal. After calculation with Bliss method by DASTM statistical software, the results of acute toxicity test in mice are shown in Table 7.

TABLE 7

Results of acute toxicity test in mice

| Extracts | $LD_{50}$(mg/kg) |
| --- | --- |
| Extract of Example 1 | 954.64 |
| Extract of Example 2 | 986.34 |
| Extract of Example 3 | 700.56 |
| Extract of Example 4 | 800.37 |
| Extract of Comparative Example 4 | 560.05 |
| Extract of Comparative Example 3 | 525.24 |
| Extract of Comparative Example 1 | 480.13 |
| Extract of Comparative Example 2 | 476.54 |
| Extract of Comparative Example 5 | 462.13 |

It can be seen from Table 7 that the LD50 value of the *Piper laetispicum* extracts of the present invention is higher than that of the comparative examples, indicating that the safety of the extract of the present invention is significantly higher than that of the Comparative Examples 4 and 3, and is also higher than the extracts of the prior art.

The above describes the present invention in detail, and its purpose is to enable those skilled in the art to understand the content of the present invention and implement it, but it cannot limit the scope of protection of the present invention. Anything change or modification based on the spirit of the present invention should be covered within the scope of protection of the present invention.

What is claimed is:

1. A *Piper laetispicum* extract comprising at least:
   N-isobutyldec-trans-2-trans-4-dienamide;
   (2E,4E)-N-isobutyldodecane-2,4-dieneamide;
   (2E,4E)-N-isobutyl-15-phenylpentadeca-2,4-dieneamide;
   (2E,4E, 14Z)—N-isobutyleicosane-2,4,14-trienamide; and
   (2E,4E)-N-isobutyl-13-phenyltrideca-2,4-dieneamide.

2. The *Piper laetispicum* extract according to claim 1, further comprising any one or more of:
   3',4'-methylenedioxycinnamic acid isobutylamide;
   (2E,6E)-N-isobutyl-7-(3,4-methylenedioxyphenyl) heptadienamide; and
   sesamin.

3. The *Piper laetispicum* extract according to claim 2, further comprising 5'-methoxy-3',4'-methylenedioxycinnamic acid isobutylamide.

4. A preparation method of the *Piper laetispicum* extract according to claim 1, comprising steps as follow:
   step (1): after pretreatment of a *Piper laetispicum* material, adding a 80%-95% ethanol solution of 10-30 times the weight of said material to impregnate or percolate to obtain a crude extract;
   step (2): concentrating said crude extract obtained in step (1) to an alcohol content of 35%-45% at a concentrating temperature not exceeding 70° C.;
   step (3): loading said crude extract concentrated in step (2) onto a macroporous adsorption resin column, eluting in sequence with a 30%-50% ethanol solution and a 50%-70% ethanol solution 2-6 times the volume of said *Piper laetispicum* material, and discarding a first eluent obtained therefrom;
   step (4): eluting with a 80%-95% ethanol solution 4-8 times the volume of said *Piper laetispicum* material, collecting a second eluent obtained therefrom, concentrating the second eluent to a brown viscous extract, and vacuum drying at a temperature not exceeding 70° C. to obtain said *Piper laetispicum* extract.

5. The preparation method of the *Piper laetispicum* extract according to claim 4, wherein said *Piper laetispicum* material in step (1) is selected from an above-ground part, or the above-ground part and an underground part of *Piper laetispicum*.

6. A method for preventing, relieving or treating mental diseases, comprising administering to a subject a medicament or a health product comprising the *Piper laetispicum* extract according to claim 1.

7. The method according to claim 6, wherein said mental diseases include depression and anxiety.

8. A medicament for prevention, alleviation and treatment of mental diseases, comprising the *Piper laetispicum* extract according to claim 1.

9. A health product for relieving mental diseases, comprising the *Piper laetispicum* extract according to claim 1.

10. A composition used for preventing, relieving and treating mental diseases, comprising at least:
    N-isobutyldec-trans-2-trans-4-dienamide;
    (2E,4E)-N-isobutyldodecane-2,4-dieneamide;
    (2E,4E)-N-isobutyl-15-phenylpentadeca-2,4-dieneamide;
    (2E,4E, 14Z)—N-isobutyleicosane-2,4,14-trienamide; and
    (2E,4E)-N-isobutyl-13-phenyltrideca-2,4-dieneamide.

11. The composition according to claim 10, further comprising any one or more of:
    3',4'-methylenedioxycinnamic acid isobutylamide;
    (2E,6E)-N-isobutyl-7-(3,4-methylenedioxyphenyl) heptadienamide; and
    sesamin.

12. The composition according to claim 11, further comprising 5'-methoxy-3',4'-methylenedioxycinnamic acid isobutylamide.

* * * * *